United States Patent [19]

Kitchin

[11] Patent Number: 4,545,030

[45] Date of Patent: Oct. 1, 1985

[54] SYNCHRONOUS CLOCK STOPPER FOR MICROPROCESSOR

[75] Inventor: David A. Kitchin, Seabrook, Md.

[73] Assignees: The John Hopkins University, Baltimore, Md.; Intec Systems, Inc., Pittsburgh, Pa.

[21] Appl. No.: 425,668

[22] Filed: Sep. 28, 1982

[51] Int. Cl.[4] .............................................. G06F 1/04
[52] U.S. Cl. .................................................... 364/900
[58] Field of Search ... 364/200 MS File, 900 MS File

[56] References Cited

U.S. PATENT DOCUMENTS

| 3,535,560 | 10/1970 | Cliff | 364/200 |
| 3,941,989 | 3/1976 | McLaughlin | 364/900 |
| 4,080,659 | 3/1978 | Francini | 364/200 |
| 4,158,230 | 6/1979 | Washizuka | 364/707 |
| 4,279,020 | 7/1981 | Christian | 364/900 |
| 4,435,761 | 3/1984 | Kimoto | 364/200 |
| 4,479,191 | 10/1984 | Nojima et al. | 364/900 |

Primary Examiner—James D. Thomas
Assistant Examiner—David Y. Eng
Attorney, Agent, or Firm—Fleit, Jacobson, Cohn & Price

[57] ABSTRACT

A synchronous clock stopper circuit for inhibiting clock pulses to a microprocessor in response to a stop request signal, and for reinstating the clock pulses in response to a start request signal thereby to conserve power consumption of the microprocessor when used in an environment of limited power. The stopping and starting of the microprocessor is synchronized, by a phase tracker, with the occurrences of a predetermined phase in the instruction cycle of the microprocessor in which the I/O data and address lines of the microprocessor are of high impedance so that a shared memory connected to the I/O lines may be accessed by other peripheral devices. The starting and stopping occur when the microprocessor initiates and completes, respectively, an instruction, as well as before and after transferring data with a memory. Also, the phase tracker transmits phase information signals over a bus to other peripheral devices which signals identify the current operational phase of the microprocessor.

4 Claims, 3 Drawing Figures

SYNCHRONOUS CLOCK STOPPER FOR MICROPROCESSOR

The invention described herein was made in the performance of work under NASA Contract No. NDPR S63742-B and is subject to the provisions of Section 305 of the National Aeronautics and Space Act of 1958 (72 Stat. 435; 42 U.S.C. 2457).

BACKGROUND OF THE INVENTION

This invention relates to microprocessor systems, and more specifically, to a clocking control circuit for controlling the operation of a microprocessor used in a power-limited environment, such as in a medical implanted device.

Among many uses of miniature electronic data processors, more commonly known as microprocessors, is to control monitoring and diagnosing circuits in implanted medical devices. They are particularly desirable because of their relatively small weight and size. In each application, however, the microprocessor requires a certain amount of power and the power demand varies according to the amount of "processing" activity performed by the microprocessor. By "processing" activity, it is meant data transfers into and out of various registers in the microprocessor and computations or logic operations performed by the processor. For use in medically implanted devices, a storage battery usually provides the source of power for the microprocessor operation, but if the battery becomes exhausted, then it becomes necessary to surgically replace the battery to maintain the electrical functions performed by the microprocessor.

One obvious approach for minimizing the foregoing difficulties is to employ microprocessor logic requiring a minimum amount of power and/or to employ extended-life, durable batteries. The advantage gained by these techniques are limited by the state-of-the-art in solid state logic and battery design. Another rather obvious approach for extending the useful life of the microprocessor power source is to turn-off power to non-essential circuits at certain time periods that do not require the affected electronic circuit, but in the case of a microprocessor controlled device, such as a data acquisition device, this may not always be possible since internal housekeeping functions require continuous operation for timekeeping, data logging, and other monitoring and control operations. Also, some types of logic circuits essential to the operation of the processor unit, such as an active memory, require repetitive refreshing cycles in order to retain the validity of their data content. Refreshing cycles requires continuous power which cannot be temporarily suspended. A significant amount of power, however, could be conserved by deactivating the processor during idle periods, such as between transfers of memory data or executions of instructions. But since the microprocessor itself is usually the sole unit within a data processing system that controls all other devices (such as peripherals and memories), it is not ordinarily powered down as synchronism in operation with the other devices could be lost.

In view of the foregoing, an objective of the present invention is to provide a clocking control circuit for reducing power requirement of a microprocessor operated in a power-limited environment.

A more specific objective of the present invention is to provide a clocking control circuit for starting and stopping a microprocessor clock at an optimum phase during its instruction cycle, thereby to reduce power drain during idle periods and to preserve its synchronism with other devices when restarted.

A further objective of the present invention is to provide a clocking control circuit for use in a microprocessor system that includes a random access memory which circuit enables the use of the memory by other peripheral devices in the system when the microprocessor is idle.

Other objects of this invention will become apparent upon review of the succeeding description of an illustrative embodiment.

SUMMARY OF THE INVENTION

In accordance with this invention, the above-mentioned and further objectives are accomplished by means of a clocking control circuit coupled to the microprocessor system which includes (1) a phase tracker for generating a phase pulse in response to an instruction cycle sync signal from the microprocessor, each sync pulse identifying a predetermined phase in the operational cycle of execution of an instruction by the microprocessor, and (2) a start/stop logic circuit responsive to the phase pulse from the phase tracker and a stop/start request signal from various devices in the microprocessor system for enabling or disabling, respectively, the flow of clock pulses from a clock source to the microprocessor. In one instance, the stop and start request signals occur between direct memory accesses by the microprocessor. In another instance, a stop request is made after the microprocessor completes an instruction cycle and a start request is made when the microprocessor initiates an instruction cycle. Starting and stopping of the microprocessor occur only with the occurrences of the phase pulse, that is, at a time when the microprocessor's I/O data lines are logically disconnected from an external peripheral bus having a device, such as a memory, connected thereto.

Advantageously, other peripheral devices may gain access to the memory while the microprocessor is disconnected. Further, the phase tracker also generates phase information signals and transmits them over a data bus thereby to inform peripheral devices connected to the data bus of the current phase of the microprocessor's instruction cycle so that the peripheral devices may ready themselves for an I/O data transfer with the shared memory.

The invention, though, is pointed out with particularity in the appended claims. The above and further objects and advantages of this invention may be better understood by referring to the following description of an illustrative embodiment of the invention taken in conjunction with the accompanying drawings.

DESCRIPTION OF ILLUSTRATIVE EMBODIMENT

As previously stated, this invention is useful for conserving power consumed by a microprocessor being operated in an environment of limited power, such as for example, in a medical implanted device. In developing this invention, it was recognized that there exists a rather significant difference in power dissipation between the static and dynamic modes of operation of a microprocessor, especially a microprocessor employing CMOS logic circuitry, such as, for example, an 1802 microprocessor manufactured by RCA.

Figure 1:
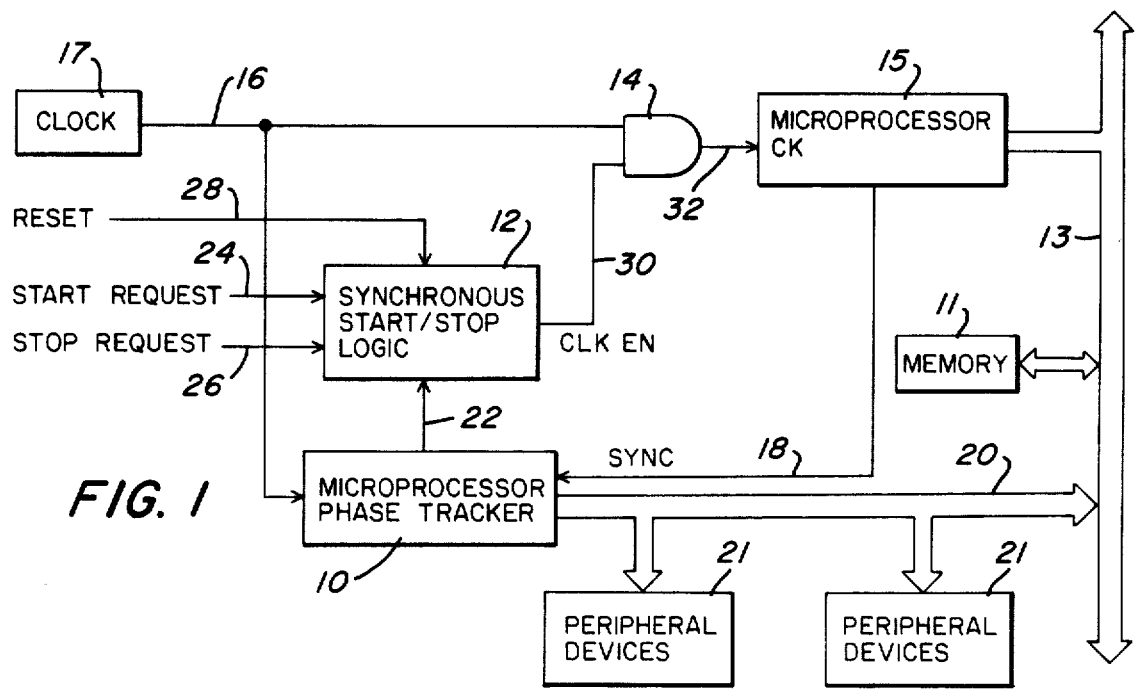
FIG. 1 is a block diagram of a clocking control circuit embodying the concepts of this invention.
Figure 2:
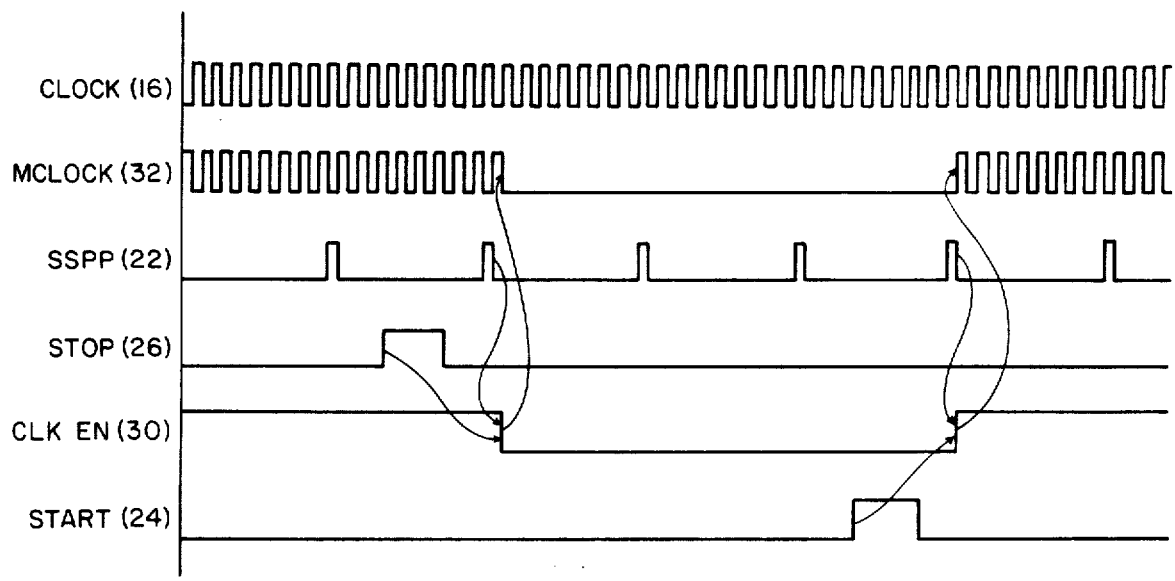
FIG. 2 is a timing diagram of the clocking control circuit of FIG. 1.

FIGS. 1 and 2 depict a block diagram circuit together with its timing diagram in which the concept of this invention may be implemented. As shown, a synchronous stop logic circuit 12 asserts a CLK EN signal on line 30 during the active, dynamic mode of operation of a microprocessor 15 and deasserts the CLK EN signal during the static inactive mode of operation. The assertion of the CLK EN signal enables an AND gate 14 which allows clocking signals to pass from a clock source 17 directly to the CK input of the microprocessor 15. While being clocked by these clocking signals, microprocessor 15 processes data transferred among the microprocessor 15, memory 11, and peripherals 21. A processor bus 13 couples the memory 11 and peripheral bus 20 couples the peripheral devices to the processor bus 13. Memory 11 typically is a random access memory having both address and data lines. It could also be another type of storage device. Peripheral bus 20 normally carries signals from data acquisition probes.

For its contemplated use in a medical implanted device about ninety percent of the microprocessor 15 activity, usually is consumed in making memory references and transfers among devices connected to the buses 13 and 20. At times, however, the microprocessor 15 is not involved in a data processing or data transfer operation and thus does not require operating power to sequence its internal registers and arithmetic units. These circumstances could be occasioned by the performance of data acquisition by one of the peripheral devices 21 which would place in the memory 11 sampled data for later use by the microprocessor 15. In the preferred embodiment, such transfer occurs while the data lines of the processor are logically disconnected from the bus 13 so that the address and data lines of the memory 13 are free.

In operation, a phase tracker 10 keeps track of the current phase of operation of the microprocessor during its instruction cycle. In the preferred 1802 microprocessor, each instruction cycle has eight stages, or phases, that run the duration of eight clocking pulses from the clock source 17. The phase tracker 10 monitors clocking pulses 16 from the clock source 17 and a sync signal 18 from the microprocessor 15. The sync signal occurs at a predetermined one of the eight phases in the operational cycle of the microprocessor 15. In synchronism with the clocking pulses and the sync pulses, the phase tracker 10 produces a series of information signals on the bus 20. These information signals inform the peripheral devices of the current instruction cycle the microprocessor 15 is undergoing. The phase tracker 10 also produces a start/stop phase pulse (SSPP pulse) on conductor 22 and supplies it to the synchronous start/stop logic 12. The SSPP pulse occurs at a predetermined one of the phases in the instruction cycle of the microprocessor 15, also in synchronism with the clock pulses from source 17. During assertion of the SSPP pulse, the data lines of the microprocessor are in a high impedance state so that, if necessary, the peripheral devices can gain access to the memory bus while the microprocessor is dormant, as previously explained.

Also, during assertion of the SSPP pulse, the synchronous start/stop logic 12 can respond to a stop request (STOP) or a start request (START) signal appearing on conductors 24 and 26. The START or STOP signals may emanate from the microprocessor 15, such as when it initiates an interrupt or completes a memory transfer. If the circuit 12 receives a STOP signal, the CLK EN signal appearing on line 30 will become deasserted at the occurrence of the next SSPP pulse. Likewise, if the processor is dormant, the logic circuit 12 will assert the CLK EN signal in response to a START signal on line 24 upon the occurrence of the next SSPP pulse from the phase tracker 22. Thus, the phase tracker 10 assures that the microprocessor always goes dormant, or becomes active, in synchronism with the desired phase in the instruction cycle of the microprocessor 15, e.g., when the microprocessor 15 is logically decoupled from the bus 13.

A RESET signal initializes all latches and gates in the synchronous start/stop logic 12 prior to operation of the circuit 12. This provides for placing the circuit 12 in operating condition when the microprocessing system is first powered up.

Figure 3:
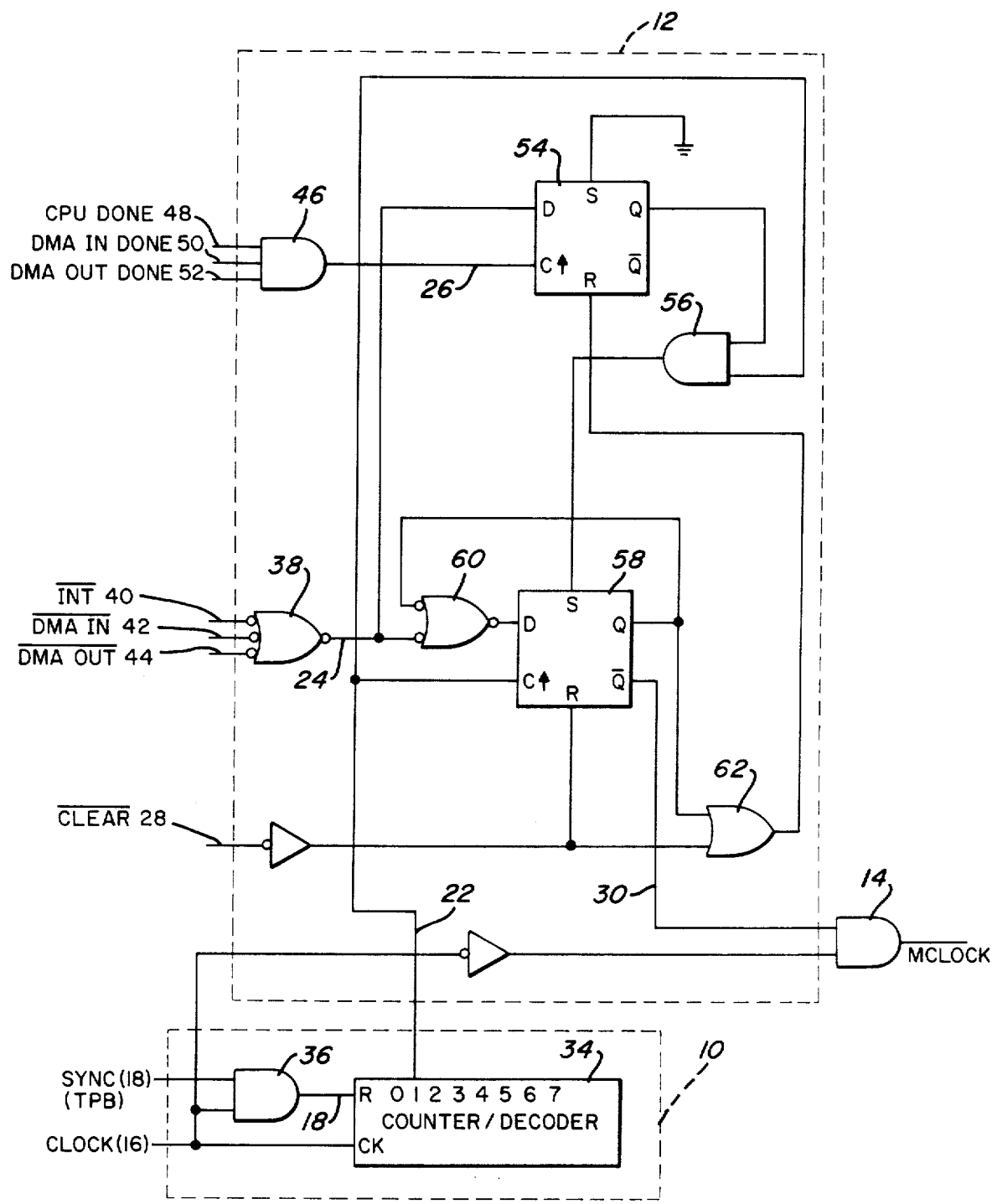
FIG. 3 is a detailed circuit diagram of the circuit of FIG. 1.

FIG. 3 shows a detail circuit diagram of the synchronous clock stopper circuit 12 and the phase tracker circuit 10 just described with reference to FIG. 1. The phase tracker 10 contains an octal counter (e.g., ring counter) and decoder circuit 34 which indexes one bit position in response to receipt of each clocking pulse from the clock source 17 (FIG. 1). In response to the clocking pulses, the decoder circuit 34 produces the SSPP pulse each time it counts eight pulses, or each time a count bit recirculates to position "one" in the ring counter 34. At phase "one" the I/O address and data lines of the microprocessor reside in a high impedence state. A SYNC signal, timing pulse "B" (TPB), from the microprocessor 15 enables one input of an AND gate 36 so that the decoder 34 is initialized (i.e., reset) at the beginning of each instruction cycle of the microprocessor 15 in synchronism with clocking pulses from the clock source 17 which also couples the other enabling input of the AND gate 36.

To initiate a start request on line 24, the synchronous start/stop logic 12 includes an OR gate 38 which responds to various control signals such as an interrupt signal "INT", and direct memory access signals "DMA IN" and "DMA OUT". These signals initiate and terminate the transfer of memory data with random access memory 11. Also, the logic circuit 12 includes an AND gate 46 which, to initiate a stop request of the processor 15 on line 26, responds to various peripheral device completion signals such as a CPU DONE, a DMA IN DONE or a DMA OUT DONE signal. These signals indicate that the processor has completed an instruction sequence or that a memory transfer operation is complete, and therefore, the processor may be stopped.

To stop the microprocessor, a flip-flop 54 is set in response to the assertion of a STOP request signal on conductor 26, assuming no START request signal is present on line 24. The "Q" output of the flip-flop 54 and the SSPP pulse on conductor 22 energize an AND gate 56 thereby to set a second flip-flop 58. The flip-flop 58 is also set upon the occurrence of the SSPP pulse. Thereafter, at its Q output, the flip-flop 58 disables an enabling signal on conductor 30 to disable the AND gate 14 thereby blocking the transfer over line 16 of the clocking pulses from the clock source 17 to the microprocessor 15. Also, flip-flop 58 asserts an enabling signal at its "Q" output which resets the flip-flop 54 through an OR gate 62, and holds itself in a set condition by virtue of an OR gate 60 connected in a feedback path of the flip-flop 58 until a START request on line 24 is made.

To restart the microprocessor 15, that is, to permit passage of the clocking signals through the AND gate 14, a START signal on conductor 24 sets the flip-flop 58 upon the occurrence of a SSPP pulse on conductor 22. When set, the "Q" output of flip-flop 58 asserts an enabling signal to enable the AND gate 14 thereby to permit passage of the clocking pulses from the clock source 17 to the microprocessor 15.

The above description illustrates a preferred embodiment of implementing the concepts of this invention, and is by no means intended to restrict the scope of the invention to that which is shown and described. It will be apparent, however, that various modifications can be made to this specific embodiment while attaining some or all of the advantages and objectives of this invention. Therefore, it is the objective of the appended claims to cover all such modifications and alternate embodiments as come within the true scope of this invention.

What is claimed is:

1. A clocking control circuit for receiving an external start request signal for a microprocessor system including a microprocessor that is responsive to clocking pulses for processing instructions in a plurality of successive stages in each instruction cycle, said microprocessor having input/output data and address lines, said clocking control circuit comprising:

a clock source for generating clocking pulses, phase tracking means coupled to said input/output data and address lines, said phase tracking means made operative by said clocking pulses for producing a phase pulse signal at a predetermined phase in each instruction cycle of said microprocessor, said predetermined phase of said phase tracking means occurring when said input/output data and address lines of said microprocessor are operating at high impedance;

means for generating a start signal based upon said external start request signal;

receiving means for receiving a stop request signal from said microprocessor system, said stop request signal being generated when said microprocessor completes an instruction sequence; and synchronous logic means responsive to said phase pulse signal and said stop request for preventing the transfer of said clocking pulses from said clock source to said microprocessor, and responsive to said phase pulse signal and said start signal for permitting the transfer of said clocking pulses from said clock source to said microprocessor.

2. A clocking control circuit as recited in claim 1 wherein said microprocessor system includes peripheral devices, the clocking control circuit including means for transmitting to said peripheral devices said phase pulse signals identifying the current phase of the instruction cycle of said microprocessor and indicating access to said input/output data and address lines.

3. A clocking control circuit as recited in claim 2 wherein said microprocessor system includes memory means common to both said microprocessor and said peripheral devices, said phase pulse signals indicating permission for data transfers to occur between said microprocessor and said memory and between said peripheral devices and said memory when said microprocessor is being clocked and between said peripheral devices and said memory means when said microprocessor is not being clocked.

4. A clocking control circuit as recited in claim 1 wherein said microprocessor system includes memory means having address and data lines and said stop request signal is generated upon completion of a data transfer between said microprocessor and memory means and said start request signal is generated in response to the initiation of a data transfer with said memory means.

* * * * *